United States Patent [19]

Ling

[11] Patent Number: 4,808,931
[45] Date of Patent: Feb. 28, 1989

[54] CONDUCTIVITY PROBE

[75] Inventor: Sung C. Ling, Silver Spring, Md.

[73] Assignee: General Technology, Inc., Silver Spring, Md.

[21] Appl. No.: 37,817

[22] Filed: Apr. 13, 1987

[51] Int. Cl.$^4$ .................... G01N 27/02; G01N 27/20
[52] U.S. Cl. .................................. 324/444; 324/449; 324/448; 324/439
[58] Field of Search ............... 324/442, 444, 446, 448, 324/450, 439, 64, 432, 437, 438, 449

[56] References Cited

U.S. PATENT DOCUMENTS

| | | |
|---|---|---|
| 3,419,796 | 12/1968 | Brown . |
| 3,474,330 | 10/1969 | Dauphinee .......................... 324/449 |
| 3,491,287 | 1/1970 | Brown . |
| 3,510,761 | 5/1970 | Brown . |
| 3,549,989 | 12/1970 | Brown . |
| 3,601,693 | 8/1971 | Lorentzen . |
| 3,774,105 | 11/1973 | Henning et al. .................... 324/437 |
| 3,936,056 | 12/1975 | Brown . |
| 3,939,408 | 2/1976 | Brown . |
| 4,227,151 | 10/1980 | Ellis et al. ......................... 324/448 |
| 4,683,435 | 7/1987 | Blades ............................... 324/442 |

*Primary Examiner*—Reinhard J. Eisenzopf
*Assistant Examiner*—Maura K. Rogan
*Attorney, Agent, or Firm*—Burns, Doane, Swecker & Mathis

[57] ABSTRACT

A four-electrode open-cell conductivity sensor for measuring the conductivity of ocean water. A simplified version of the conductivity sensor may be used as a standard conductivity cell for measurement of fluid conductivity in a laboratory, or for monitoring fluid conductivity in a chemical processing plant. The sensor includes opposed electrode pairs each of which include a hemispherical current electrode and a coaxial ring-shaped voltage electrode. In operation, an alternating current is generated across the opposed current electrodes and the resultant electric field is sensed by the voltage electrodes. A feedback circuit is utilized to adjust the amplitude of the electric current generated across the current electrodes so that the inphase potential across the voltage electrodes is maintained at a substantially constant level. The conductivity of the fluid between the opposed electrode pair can be obtained directly from the current flowing across the current electrodes without the need for precalibrating the sensor against known conductivity standards.

20 Claims, 6 Drawing Sheets

CONDUCTIVITY PROBE

The U.S. Government has a paid-up license in this invention and the right in limited circumstances to require the patent owner to license others on reasonable terms as provided for by the terms of contract No. N00024-81-C-5301 awarded by the United States Department of the Navy.

BACKGROUND OF THE INVENTION

The present invention relates to a sensor probe for determining the conductivity of a fluid. More particularly, the present invention relates to a non-fouling, open-cell four electrode conductivity sensor for oceanic use.

Conductivity sensors have previously been developed for use in monitoring oceanic environmental conditions and other research applications. For example, an array of sensors may be positioned along a cable towed by a surface ship so as to monitor environmental conditions of the water below the surface ships. Sensor arrays may also be towed by submarines. However, such prior art sensors have several drawbacks relating to measurement accuracy and fouling by biological matter, such as seaweed.

A typical example of the prior art is U.S. Pat. No. 3,601,693 to Lorentzen which discloses a four electrode closed-cell conductivity measuring device. The measuring cell includes a pair of current electrodes and a pair of voltage electrodes. The current electrodes are connected in series with an alternating current source and a current measuring device. The voltage electrodes are connected to a voltage measuring device. A ratio of the measured current flow to the measured voltage provides an indication of the electrolytic conductivity of the fluid contained in the measuring device.

U.S. Pat. No. 3,939,408 issued to Brown relates to a T-shaped four electrode closed-cell conductivity probe. The probe includes a pair of voltage electrodes and a pair of current electrodes. The voltage electrodes are connected in the input circuit of a high gain amplifier which has a negative feedback loop in which the current electrodes are connected. The feedback control circuit tends to maintain at all times the voltage at a value equal the reference voltage. The ratio of the amplitude of the feedback current and the AC reference signal is linearly proportional to the conductivity of the fluid within the cell.

Closed-cell probes of the type described above have inherent drawbacks relating to fouling, a high degree of flow distortion, poor flushing, large signal drift, poor dynamic response, relatively large dead band, cross-circulation, potential field complexity, and angle-of-attack sensitivity. Accordingly, these devices have not proven to be completely acceptable in practice.

Two electrode configurations have also been developed which have the advantage of an open-cell configuration. These devices, however, are relatively unstable, include a high electronic noise level that may interfere with neighboring instrumentation, are serious affected by biological material present in the fluid being tested, draw large electric currents, and are of questionable durability.

It has been necessary to provide an accurate and efficient conductivity probe, for use in oceanic application, which is not prone to fouling from biological materials. Accordingly, it is a primary object of the present invention to provide a highly accurate and efficient non-fouling conductivity probe which overcomes the foregoing disadvantages.

BRIEF SUMMARY OF THE INVENTION

The present invention generally relates to a four electrode open-cell conductivity sensor which includes two electrode pairs mounted in opposition. Each electrode pair preferably includes a hemispherical current electrode and a ring-shaped voltage electrode mounted coaxially with the current electrode. A fluid to be tested flows between the electrode pairs for a conductivity measurement. The open-cell probe mount is designed to avoid fouling by sea weed and other biological matter in the ocean. In operation, an alternating current is developed across the current electrodes and the resultant potential field is sensed by the ring voltage electrodes. The in-phase potential across the voltage electrodes is maintained substantially constant by regulating the amplitude of the electric current that flows between the current electrodes. This is accomplished by means of a feedback control circuit. The current required to maintain the substantially constant in-phase potential across the voltage electrodes is linearly proportional to the conductivity of the fluid. The electric field produced by the probe permits the conductivity measurement to be free from surface contamination and polarization effects. Additionally, the probe is free from the slow diffusion effect of the boundary layer flow near the surfaces of the electrodes. By providing current electrodes with a hemispherical structure, uniform current flux and uniform minimum potential gradient over the surface of the electrodes are provided to minimize effects due to surface contamination.

BRIEF DESCRIPTION OF THE DRAWINGS

The objects, features, and advantages of the present invention will become readily apparent to the skilled artisan from the following detailed description when read in light of the accompanying drawings, in which.

DETAILED DESCRIPTION OF THE PREFERRED EMBODIMENT

In the following detailed description, the conductivity probe will be described in connection with an application in which the conductivity of sea water is measured. It will be readily appreciated, however, that a simplified version of the conductivity sensor may be used as a standard conductivity cell for measurement of fluid conductivity in a laboratory or for monitoring fluid conductivity in a chemical processing plant.

Figure 1:
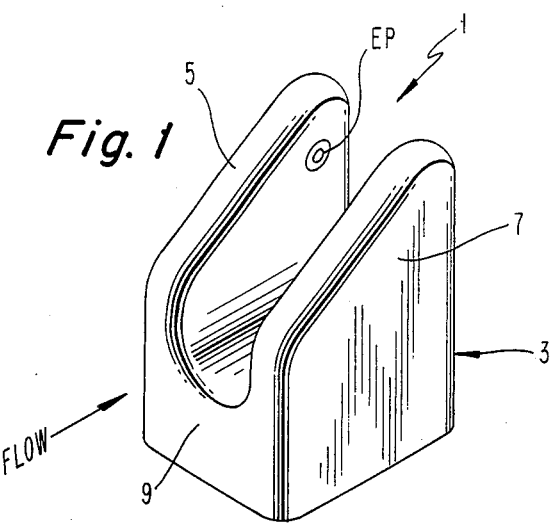
FIG. 1 is a perspective view of a probe construction in accordance with the present invention.

Referring to FIG. 1, a probe 1 includes a body portion 3 having first and second opposed upstanding arm portions 5 and 7, respectively, and a base portion 9. The probe body is preferably formed of a durable, electrically insulating material such as pure alumina ceramic or a suitable plastic material. First and second electrode pairs EP are mounted in opposition to one another on the first and second upstanding arm portions 5 and 7, respectively. Only one electrode pair is illustrated in FIG. 1. In operation, a test fluid passes in the direction of the arrow in FIG. 1 through the channel defined by the upstanding arm portions 5 and 7 and base portion 9 of the probe body portion 3. The conductivity of the fluid passing through the channel may then be measured through use of the opposed electrode pairs. As shown in FIG. 1, the upstanding arm portions 5 and 7 are tapered upwardly in the direction of fluid flow. This taper helps prevent clogging of the probe by seaweed or the like.

Figure 2A:
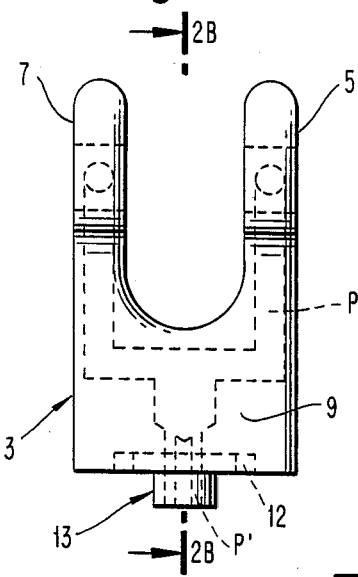
FIG. 2A is a rear view of the probe body of FIG. 1.
Figure 2B:
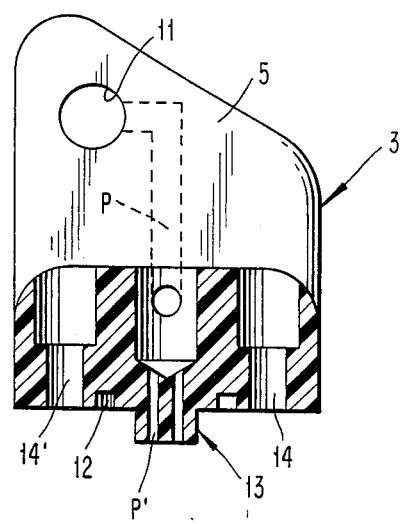
FIG. 2B is a cross-sectional view of the probe body of FIG. 1.
Figure 2C:
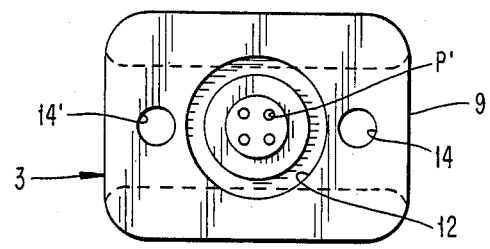
FIG. 2C is a bottom view of the probe body of FIG. 1.

Referring to FIGS. 2A-2C, the main probe body 3 may be milled out of a single block of an appropriate plastic material such as HOMALITE plastic. The probe body may also be formed by molding a material such as pure alumina ceramic, which has the advantage of being more stable than a plastic material such as HOMALITE. The material used for making the probe should have a low degree of thermal expansivity and should be relatively unaffected by other environmental effects.

Each of the opposed upstanding arm portions 5 and 7 includes an electrode-mounting aperture 11 into which an electrode assembly may be placed. The electrode assembly will be discussed below with reference to FIGS. 3A-3C. Passages P and P' are preferably provided within the probe body to permit passage of electrical conductors between the electrode assemblies and the system electronics. A rubber O-ring may be inserted in groove 12 to prevent sea water from entering the passages P and P' from A mounting portion 13 is provided for mounting the probe body. Preferably, threaded fasteners or other appropriate fasteners (not shown) are inserted through fastener passages 14 and 14' to secure the probe body to an appropriate mount.

Figure 3A:
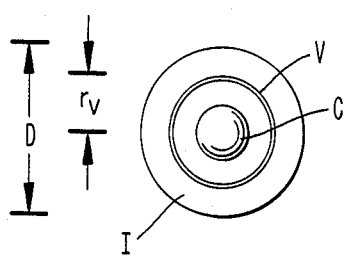
FIG. 3A is a front view of an electrode assembly adapted to be mounted in the probe body of FIGS. 2A-2C.
Figure 3B:
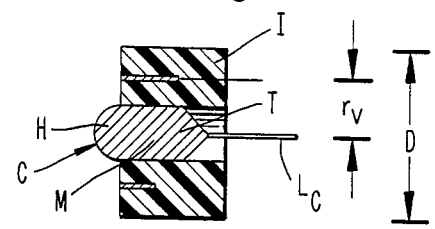
FIG. 3B is a cross-section side view of the electrode assembly of FIG. 3A.
Figure 3C:
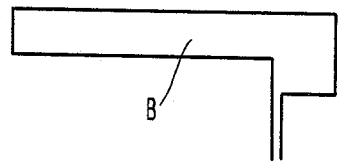
FIG. 3C illustrates a foil blank useful in producing the electrode assembly of FIGS. 3A and 3B.

The electrode assembly for mounting in each of the electrode-mounting apertures 11 of upstanding arm portions 5 and 7 is illustrated in FIGS. 3A-3C. FIG. 3A is a frontal view of the electrode assembly including a current electrode C and a ring-shaped voltage electrode V surrounding the current electrode C. The current electrode C and the voltage electrode V preferably are concentric.

As shown in FIG. 3B, the current electrode C includes a hemispherically-shaped exposed end portion H, a cylindrical main portion M, and a tapered portion T. An electrical lead $L_c$ projects from the end of the tapered portion T to permit the current electrode to be connected with the system electronics. The current electrode C is preferably formed of platinum and may be formed from platinum wires which are pressed by a hardened steel die set into hemispherical pellets. Preferably, the exposed end portion H of the current electrode is plated with a thin layer of platinum black. Platinum black is a spongy structure of pure platinum which tends to increase the effective contact area of the electrode.

An electrically insulating material such as an alumina filled epoxy material I separates the current electrode C from the voltage electrode V. As indicated in the drawing, the voltage electrode V is arranged with the insulating material at a radius $r_v$. The total diameter D of the electrode assembly generally corresponds to the inner diameter of the electrode mounting aperture 11 (FIG. 2).

The electrode assembly may be manufactured by providing an alumina filled epoxy mandrel having a radius $r_v$. A platinum foil blank such as that illustrated in FIG. 3C may then be wrapped around the periphery of the mandrel in order to form a concentric ring. The platinum foil blank may be produced by rolling and machining a platinum wire. As illustrated, the foil blank includes a lead portion $L_v$ which permits the voltage electrode to be connected with the system electronics. Alumina filled epoxy may then be cast over the platinum ring and machined to a diameter D. The material in the center of the mandrel may be removed by drilling in order to provide an opening into which the current electrode C is inserted. The portion of the voltage electrode that will be exposed to the test fluid is preferably coated with platinum black.

Production models of a probe in accordance with the present invention may be formed of a molded pure ceramic material. The electrodes for the production models may be formed by plating and photoetching processes. Preferably, the voltage electrodes are formed by a thick film technique or other appropriate technique which permits the voltage electrodes to have a relatively small difference between the inner diameter and the outer diameter.

Figure 4:
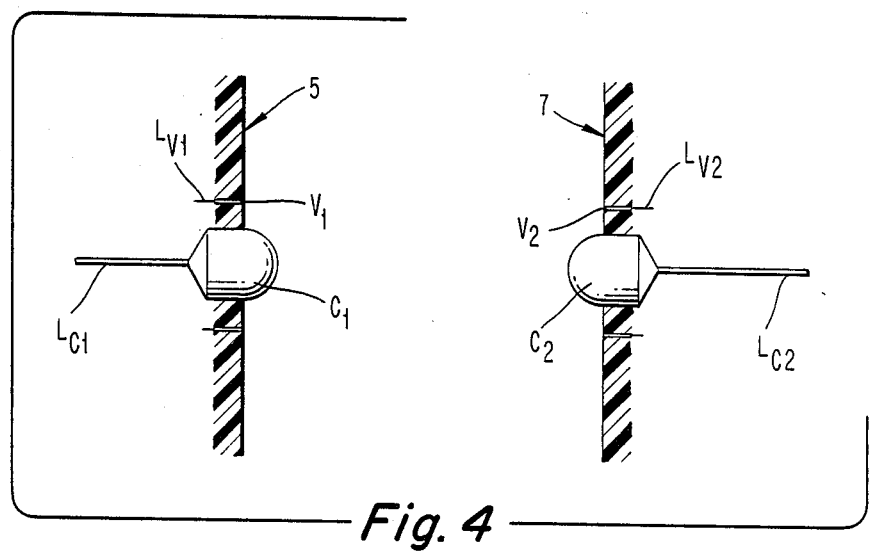
FIG. 4 is a cross-section view illustrating the details of the electrode structure of the probe of FIG. 1.

FIG. 4 illustrates the probe electrodes in their assembled configuration. Current electrode $C_1$ and voltage electrode $V_1$ are mounted on upstanding arm portion 5. Leads $L_{c1}$ and $L_{v1}$ are provided to connect the current electrode $C_1$ and the voltage electrode $V_1$, respectively, to the system electronics. Current electrode $C_2$ and voltage electrode $V_2$ are mounted on upstanding arm portion 7 in opposition to current electrode $C_1$ and voltage electrode $V_1$, respectively. Leads $L_{c2}$ and $L_{v2}$ are provided to connect the current electrode $C_2$ and the voltage electrode $V_2$, respectively, to the system electronics.

During operation, an alternating current I is developed by the application of a 10 KHz low potential of 0.2 $V_{RMS}$ across the current electrodes $C_1$ and $C_2$. The alternating current minimizes electrolysis effects on the liquid under testing. The potential field established in the liquid medium is sensed by the two equipotential ring electrodes $V_1$ and $V_2$. The in-phase potential across electrodes $V_1$ and $V_2$ is maintained substantially constant at a fixed value, for example 0.1000 $V_{RMS}$, by regulating the current I through a feedback control circuit. The feedback control circuit will be described in detail with reference to FIG. 8. The current I which flows between the current electrodes $C_1$ and $C_2$ is linearly proportional to the conductivity $\sigma$ of the fluid; i.e., $$\sigma = KI \quad (1)$$

where K is the gauge constant of the sensor. As will be discussed more fully below, the value of the gauge constant K may be derived analytically.

Figure 5:
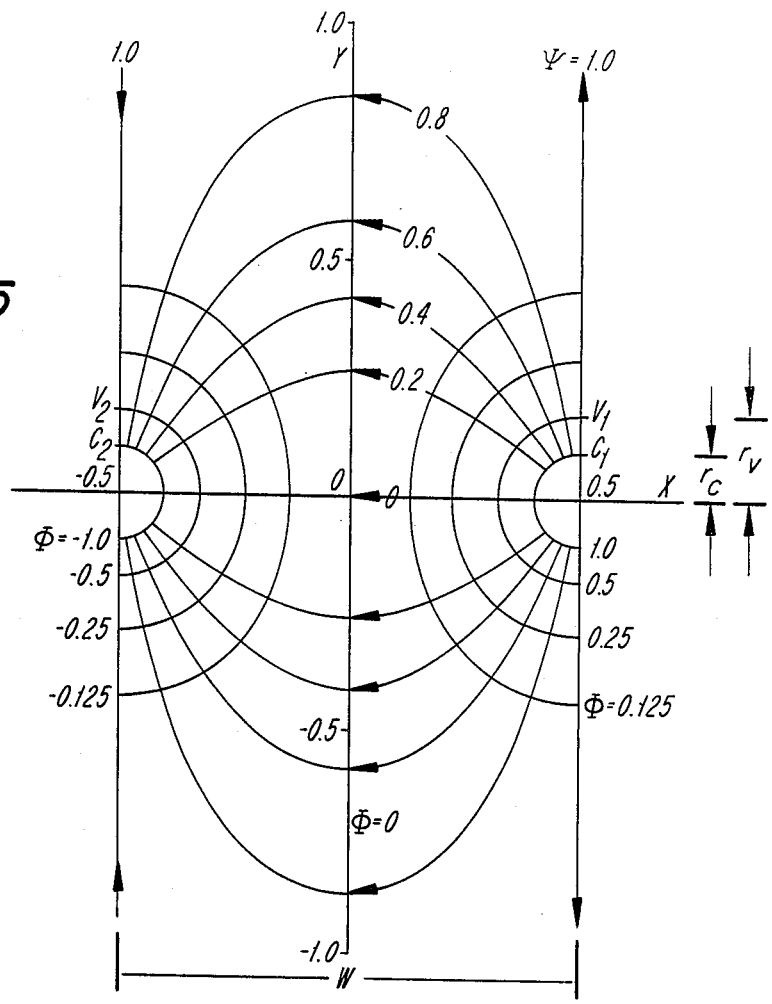
FIG. 5 illustrates the electric field generated with the electrode structure illustrated in FIG. 3.

Referring now to FIG. 5, a Cartesian coordinate system having an x-axis and a y-axis will be used to explain the electric field generated by the probe of the present invention. The electric field produced by the current electrodes $C_1$ and $C_2$ can be simulated by an infinite number of sets of current sources $+q$ and sinks $-q$ distributed along the x-axis containing the centers of the current electrodes $C_1$ and $C_2$. The width of the sensor W is the distance between the centers of the hemispherical current electrodes $C_1$ and $C_2$. All linear dimensions may be normalized by W, hence current electrodes $C_1$ and $C_2$ are located at the normalized position $X = x/W = 0.5$ and $-0.5$, respectively, where x is the x-axis coordinate in the Cartesian coordinate system. A current source $+q$ is placed along the x-axis at each of the following locations: $X = 0.5, 2.5, 4.5, \ldots,$ and $-1.5, -3.5, -5.5, \ldots$; similarly a current sink $-q$ is located at $X = -0.5, -2.5, -4.5, \ldots,$ and $1.5, 3.5, 5.5, \ldots$ The potential field produced by these fluxes will provide the required electric field between the two current electrodes of the sensor. The distribution of pairs of sources and sinks at $X > 0.5$ and $X < 0.5$ is necessary to produce the required boundary condition of zero current flux across the insulating surfaces of the probe mounts; i.e., $$\left.\frac{d\phi}{dX}\right|_{X=\pm 0.5} = 0,$$

where $\phi$ is the potential. The resulting potential field contributed by the distributed sources and sinks is axially symmetrical about the x-axis. Hence, the field in the meridional xy-plane will represent the three-dimensional field. In this plane, the potential of the flow field can be expressed as:

$$\phi = \sum_{n=1}^{\infty} \frac{q}{4\pi\sigma W} \left( \frac{1}{\sqrt{(X-n+0.5)^2 + Y^2}} - \frac{1}{\sqrt{(X+n-0.5)^2 + Y^2}} \right)(-1)^n, \quad (2)$$

where $\sigma$ is the conductivity of the fluid, and $Y = y/W$. In general, it is possible to obtain sufficient results by summing only over a predetermined number of values for n. For example, equation (2) might only be calculated for values of n from 1 to 80.

The invention contemplates that the current electrodes $C_1$ and $C_2$ are made with a normalized radius $\bar{r}_c = r_c/W = 0.10$. Hence, with $X = 0.40$ and $Y = 0$ in equation (2), the potential $\phi_{c1}$ at the surface of electrode $C_1$ is $$\phi_{c1} = 8.595 \frac{q}{4\pi\sigma W}. \quad (3)$$

Normalizing Eq. 2 by Eq. 3, $$\Phi = \frac{\phi}{\phi_{c1}} = \frac{1}{8.595} \sum_{n=1}^{\infty} \left( \frac{1}{\sqrt{(X-n+0.5)^2 + Y^2}} - \frac{1}{\sqrt{(X+n-0.5)^2 + Y^2}} \right)(-1)^n. \quad (4)$$

The solutions to Eq. 4 for different constant values of $\Phi$ are shown in FIG. 5. Note that the normalized potentials $\Phi$ at $C_1$ and $C_2$ are by definition equal to 1.0 and $-1.0$, respectively; and $\Phi = 0$ at $X = 0$. Preferably, the equipotential voltage electrodes $V_1$ and $V_2$ are circular rings with normalized radius $\bar{r}_v = r_v/W = 0.177$ and are concentric to current electrodes $C_1$ and $C_2$, respectively. From FIG. 5, the corresponding $\Phi_{v1}$ and $\Phi_{v2}$ are 0.50 and $-0.50$, respectively, thus, with $\bar{r}_v/\bar{r}_c = 1.77$, and $\Phi_v/\Phi_c = 0.50$.

Similarly, one may solve for the stream lines of force. By Gauss's electric flux theorem, the stream line $\psi$ can be expressed as $$\psi = \sum_{n=1}^{\infty} q \left( \frac{X-n-0.5}{\sqrt{(X-n+0.5)^2 + Y^2}} - \frac{X+n-0.5}{\sqrt{(X+n-0.5)^2 + Y^2}} \right)(-1)^n. \quad (5)$$

The stream function is further normalized by the flux q as $$\Psi = \frac{\psi}{q} = \sum_{n=1}^{\infty} \left( \frac{X-n+0.5}{\sqrt{(X-n+0.5)^2 + Y^2}} - \frac{X+n-0.5}{\sqrt{(X+n-0.5)^2 + Y^2}} \right)(-1)^n. \quad (6)$$

Normalized stream lines or stream surfaces for different constant $\psi$ are shown in FIG. 5. The stream line along the x-axis has a value of $\psi = 0$. The stream surface along the surfaces of the insulating probe mounts has a value of $\psi = 1$. Theoretically, $\psi = 1$ is infinitely long, hence no significant amount of current flows along this surface. This provides an ideal characteristic for the sensor; i.e., the probe will be insensitive to surface contamination.

Figure 6:
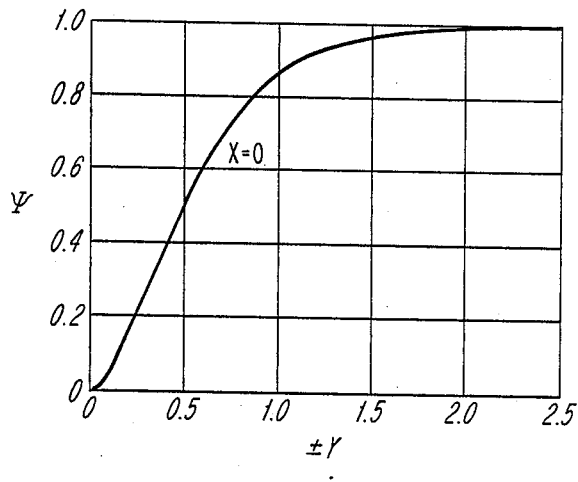
FIG. 6 illustrates the distribution of the stream lines of force along the central plane of symmetry of a conductivity probe in accordance with the present invention.

The distribution of $\psi$ along the central plane of symmetry $(X = 0, Y)$ is shown in FIG. 6. Here, the function of $\psi$ is plotted with respect to Y. Note, that by definition, $\psi$ represents the integral value of current flux. The flux between $\psi = 0$ and $\psi = 1$ stream tubes contains all the fluxes q from electrode $C_1$. It should be noted that only half (q/2) of the total flux flows within the sensor volume, as shown in FIG. 5. The other symmetrical half of the flux field flows to the right hand side of $C_1$ and is not shown in FIG. 5. Stream tubes $\psi = 0, 0.2, 0.4, 0.6$ and 0.8 are plotted in FIG. 5. Thus, each of these tube intervals carries 1/5 of the net current flux q/2 flowing within the sensor volume.

From FIG. 6, it can be seen that a majority of the fluxes, $\psi = 0.86$ or 86%, is conducted within $Y = 1.0$, and 99% up to $Y = 2.0$. Hence, the effective sensing length of the detector can be approximately taken as 2W. This represents the spatial resolution limit of the probe. The effective volume of the fluid being measured can be assumed to be confined between the equipotential surfaces of $\Phi_{v1}=0.5$ and $\Phi_{v2}=-0.5$, and the stream tube $\psi \approx 0.8$. No part of this fluid volume is in contact with the current electrodes or any solid walls, hence the sensor is uniquely free from surface contamination and polarization effects. Additionally, the sensor is free from the slow diffusion effect of the boundary layer flow near the surfaces of the electrodes. Therefore, the sensor has a very good spatial and time resolving capability.

The hemispherical shape of the exposed portion of the current electrodes provides not only uniform surface flux, but also a uniform minimum potential gradient achievable over any electrodes. Furthermore, when the ring-shaped voltage electrodes are precisely aligned with the equipotential field of the fluid, they should be relatively free from surface contamination effects. Thus, optimal operating stability for the sensor is ensured.

Once the electrical field distribution has been determined, the gauge constant for a given sensor design may be obtained readily. By definition, the resistance R of the gauge is equal to the potential across voltage electrodes $V_1$ and $V_2$ divided by the current flux, $$R = \frac{\phi_{v1} - \phi_{v2}}{q/2} = \frac{4\phi_{v1}}{q} = \frac{2\phi_{c1}}{q}. \quad (7)$$

with Eq. 3 in Eq. 7, $$R = \frac{8.595}{2\pi\sigma W} = \frac{1.368}{\sigma W}. \quad (8)$$

Assuming that a minimum spatial resolution of 2 cm is required for detecting the microstructure of the ocean, a gauge with a width W of 1 cm would be of an appropriate size. Thus, the standard sea-water conductivity $\sigma = 5.3 \times 10^{-2}$ (ohm-cm)$^{-1}$ or 53 mmho and width W=1.00 cm, the gauge will have a typical resistance R=25.8 ohms.

For the preferred embodiment of the present invention, the conductivity of the fluid can be expressed through Eq. 8 as $$\sigma = \frac{1.368}{WE_v} I, \quad (9)$$

where $E_v$ is the potential difference between voltage electrodes $V_1$ and $V_2$. In operation, $E_v$ may be precisely regulated at a substantially constant value of, for example, 0.100 volt. Hence, the gauge constant K is by Eq. 9

$$K = \frac{1.368}{1.00 \times 0.100} = 13.68, \text{ (ohm-cm-amp)}^{-1},$$

and Eq. 1 can be expressed as $$\sigma = 13.68 \text{ I, (ohm-cm)}^{-1}, \quad (10)$$

where I is the gauge current expressed in amperes.

As discussed above, in order to obtain good spatial resolution a probe width W=1.00 cm may be chosen. Additionally, the selection of a radius of 0.10 W for the current electrodes $C_1$ and $C_2$ provides a gauge resistance R of 25.8 ohms in standard sea water. With the ring-shaped voltage electrodes operating at a substantially constant low potential of 0.1000 $V_{RMS}$, and the corresponding current electrodes at 0.200 $V_{RMS}$ to prevent chemical dissociation of the water, the typical operating current for the probe is 4 milliamps at 10 KHz. Under these low operating voltages and currents, both heating and chemical dissociation effects are reduced to levels which will not provide a serious adverse effect on the conductivity measurement.

The voltage electrodes draw essentially no current during operation of the probe. Hence, the out-of-phase voltage due to capacitive effects is small and may be cancelled by a standard common-mode rejection technique.

As indicated above, the gauge constant K is directly related to the physical size of the probe and the probe geometry. For best results, in the preferred embodiment the width of the spacing W between the electrodes should be held to 1.000±0.005 cm against all thermal and environmental influences. The thermal expansivity of HOMALITE plastic is approximately $5 \times 10^{-5}$ cm/C°. For a typical ±10° C. operating temperature range of the probe about 15° C., the dimensional change in the width W is approximately ±0.0005 cm, which is well within the permissible variation of 0.005 cm. Pure alumina ceramic has even better stability against thermal changes than does HOMALITE plastic.

The gauge constant is also directly related to the potential at the ring-shaped voltage electrodes. Therefore, the voltage electrodes should be precisely concentric with the current electrodes. In the preferred embodiment, the current electrodes should have a radius of 0.100±0.0005 cm and the voltage electrodes should have a radius of 0.177±0.001 cm. If the voltage electrode is precisely concentric with the current electrode, the voltage electrode will be arranged precisely at the equal potential ring of $\Phi_v/\Phi_c=0.500$. If the voltage electrode is slightly off-center, it will still indicate a value of $\Phi_v/\Phi_c=0.500$ due to the averaging of the potential around the ring. Under this condition, however, any occlusion over the voltage electrodes due to dirt or the like may cause a drift in the measured signal since the voltage electrode is not arranged precisely in the equipotential zone.

The degree of concentricity required to obtain an optimal measurement may be estimated by calculating the radial potential gradient, i.e. $d\Phi/dY$ at the ring-shaped voltage electrode. This can be done by taking the derivative of the nondimensional potential $\Phi$ with respect to the nondimensional Y at the ring. From Eq. 4, $$d\frac{\Phi}{dY} = \frac{Y}{8.595} \sum_{n=1}^{\infty} \{[(X - n + 0.5)^2 + Y^2]^{-3/2} - [(X + n - 0.5)^2 + Y^2]^{-3/2}\}(-1)^{n+1}. \quad (11)$$

Therefore, at the voltage electrode, X=0.5 and Y=0.177, $$\left.\frac{d\Phi}{dY}\right|_{ring} = 3.69. \quad (12)$$

Hence, for a normalized $\Phi_v$ of 1.0 a selected 1% maximum allowable deviation of $\Phi$ is $\Delta\Phi=1.0 \times 0.01=0.01$. Of course, a 1% maximum allowable deviation is chose to achieve desired measurement accuracy, and other deviation values could be likewise chosen in accordance with a different desired measurement accuracy. For example, if a maximum allowable deviation of 2% was chosen, the deviation in $\Phi$ would be $\Delta\Phi=1.0\times0.02=0.02$. The corresponding allowable deviation radial concentricity of the voltage electrode is, by Eq. 12, $\Delta Y=\Delta\Phi/3.69=0.003$, or an eccentricity $\Delta r_v$ for the ring of less than 0.003 cm. Thus the voltage electrode should be highly concentric with respect to the current electrode. Additionally, the radial width of the voltage electrode should be made as small as possible, approximately equal to $\Delta r_v$. A practical radial width of the voltage electrode of approximately 0.005 cm is possible since it is unlikely for the entire inner or outer edge of the ring to be occluded by dirt at any given point in time.

The sensor of the present invention is relatively insensitive to minor occlusion of the current electrodes. Additionally, the hemispherical shape of the exposed portion of the current electrodes provides a uniform distribution of both the potential gradient and the current flux over the surface of the electrode. Accordingly, the sensor of the preferred embodiment is much less sensitive to surface contamination than are sensors having flat current electrodes where high current fluxes are concentrated at the peripheries of the electrodes.

Figure 7:
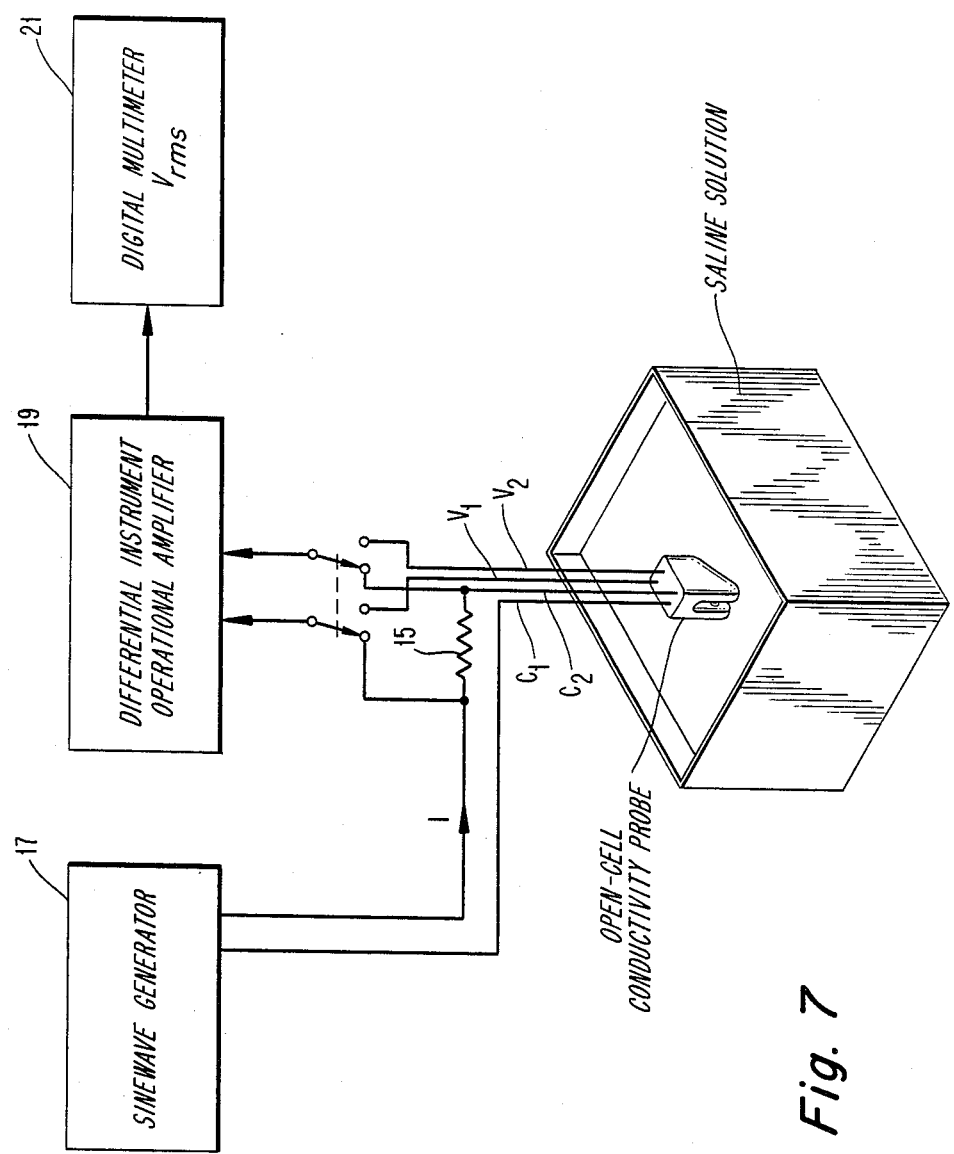
FIG. 7 is a schematic circuit diagram illustrating an experimental arrangement used to test the general operation of a probe in accordance with the present invention.

An experimental arrangement was provided to test the operation of a probe in accordance with the present invention. Referring to FIG. 7, a precision 50.00 ohm resistor 15 was connected in series with current electrodes $C_1$ and $C_2$, and the circuit was driven by a 10 KHz sine wave generator 17. A Hewlett Packard Model 3300A function generator was used to produce the sine wave signal. The voltage developed across the 50.00 ohm resistor 15 was monitored by an Ectron Model 750EL precision differential instrument operational amplifier 19 with a gain setting at $\times 1.000$. The operational amplifier 19 had an input impedance of 20 Mohms and a common rejection ratio of 80 db. The output of the amplifier 19 was monitored by a Hewlett Packard Model 5306A digital multimeter 21 which was set to operate as a voltmeter. The voltage across the ring-shaped voltage electrodes $V_1$ and $V_2$ was also monitored by the operational amplifier 19 and digital meter 21. A double pole, double throw switch 23 was provided to permit the voltage across resistor 15 and the voltage electrodes to be monitored by the same operational amplifier and digital meter.

The high common mode rejection ratio of the operational amplifier 19 effectively balanced out all common mode polarization signals and noises induced at the electrodes. Test measurements indicated no measurable phase angle between the voltage across the voltage electrodes and the current signal across the resistor 15. Thus, the detection of pure resistive data was ensured.

The test fluid representing sea water was obtained by taking an exact volume of 500 cc of distilled water and mixing it with an appropriate weight of salt to achieve a solution of known salinity. A weighing accuracy of $\pm 1$ milligram was used. The saline solution was then placed in a constant temperature bath and maintained at $20.00°\pm 0.005°$ C.

With the probe immersed in the test solution, the amplitude of the signal from sine wave source 17 was adjusted until the voltage detected across the voltage electrodes wa precisely 0.1000 $V_{RMS}$. The voltage across resistor 15 was then read, and this voltage was divided by 50 ohms to obtain the value of the current I flowing through the fluid medium. In accordance with Eq. 10, the conductivity $\sigma$ of the test fluid was then expressed through the gauge constant of the probe as $\sigma=13.68I$ (ohm-cm)$^{-1}$, where I is expressed in amperes.

The results of the test measurements are tabulated below in Table 1. As indicated in the Table, the measured conductivity values were in close agreement with the standard values for the test solutions.

TABLE 1

| 20.00° C. 1 atm $S°/_{oo}$ | New Probe Direct Measurements | | Standard $\sigma$ mmho/cm | Difference +% |
|---|---|---|---|---|
| | 1 amp | $\sigma$ mmho/cm | | |
| 20.000 | .002152 | 29.4 | 29.2 | 0.7 |
| 25.000 | .002634 | 36.0 | 35.8 | 0.6 |
| 30.000 | .003102 | 42.4 | 42.2 | 0.5 |
| 35.000 | .003562 | 48.7 | 48.4 | 0.6 |
| 40.000 | .004002 | 54.8 | 54.5 | 0.6 |

Figure 8:
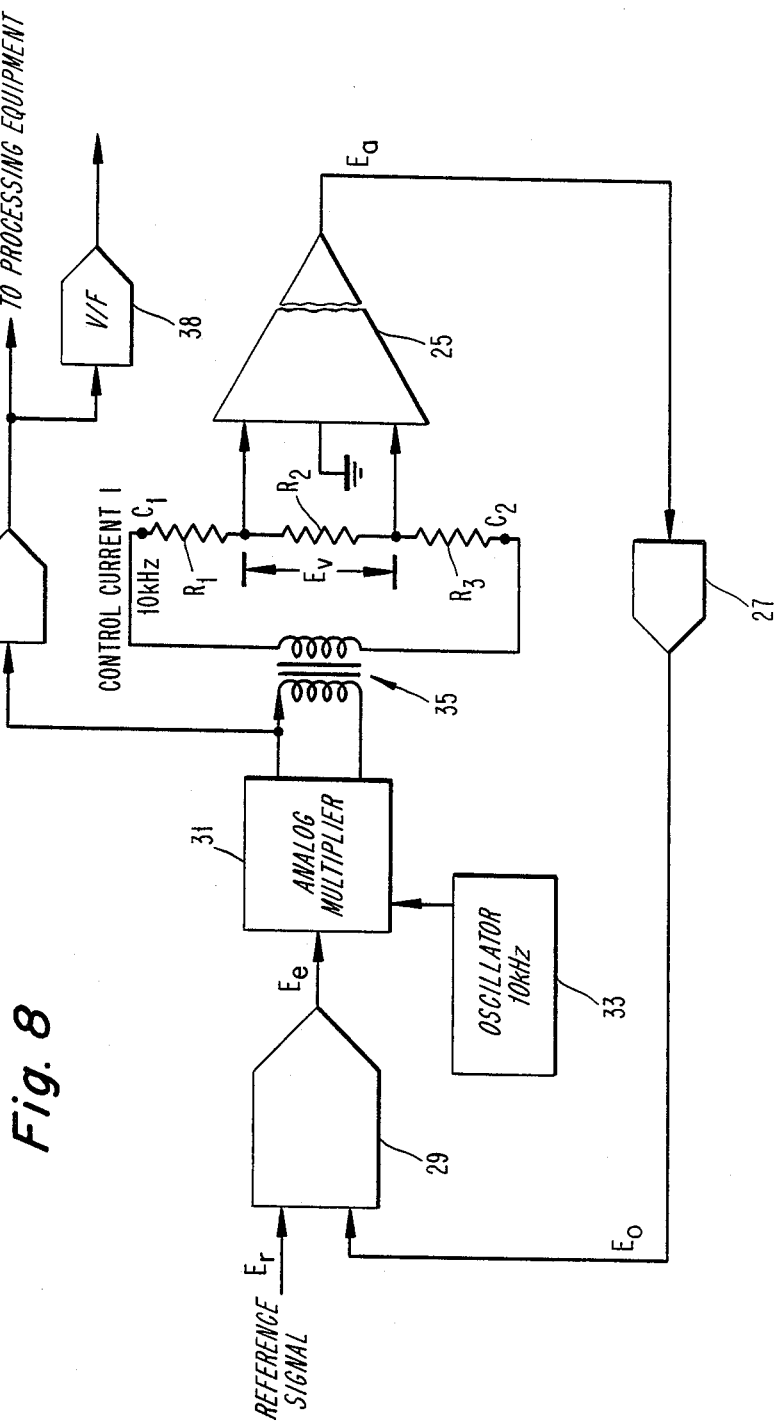
FIG. 8 is a schematic circuit diagram illustrating a control feedback system in accordance with the present invention.

FIG. 8 illustrates an equivalent electrical circuit for a conductivity probe in accordance with the present invention. The current electrodes $C_1$ and $C_2$ and the voltage electrodes $V_1$ and $V_2$ are represented by nodes in the circuit. Resistances $R_1$, $R_2$ and $R_3$ are used to represent the resistance provided by the test fluid.

As discussed previously, the sensor of the present invention is operated under a substantially constant voltage condition, with the resulting current flowing through the sensor providing an indication of the conductivity of the fluid medium being tested. For best results, it is advantageous to use a very high integral feedback control to keep the operating voltage across the voltage electrodes substantially constant for a wide range of test fluid conductivities. By having a high feedback control factor, it is also possible to obtain nearly infinite detector input impedance with good common-mode noise and polarization signal rejection.

Referring to FIG. 8, the open-cell sensor of the present invention is activated by a 10 KHz variable amplitude current I across the current electrodes $C_1$ and $C_2$. The resultant potential across the voltage electrodes $V_1$ and $V_2$ is maintained by the control system at a substantially constant voltage $E_v=0.1000$ $V_{RMS}$.

The potential across the voltage electrodes is sensed by an AC isolation operational amplifier 25 which isolates the sea ground from the remaining portions of the instrument. The amplifier 25 is preferably set for a precise gain of 10.00 and, thus, produces an output voltage $E_a=10E_v=1.000$ $V_{RMS}$ at 10 Khz. Preferably, the amplifier 25 has a high common mode rejection ratio and a high input impedance. Thus, common mode noise and polarization effects will be automatically cancelled and only the true differential signals related to the conductivity of the test fluid will be detected. In order to obtain full benefit of this feature, it is preferable to make both sets of electrodes as similar as possible. Accordingly it may be desirable to preselect matched pairs of electrodes to form the conductivity probe.

The amplifier output voltage $E_a$ is converted by a peak detector and 10 KHz filter 27 into a DC signal voltage $E_o$ which has a substantially constant value of 1.414 V. The DC signal voltage $E_o$ is then supplied to a comparator/amplifier 29 and is compared with a fixed precision DC reference voltage $E_r=1.414$ V to produce an error voltage $E_e=E_r-E_o$. The error signal is amplified by the comparator/amplifier 29 which is preferably a high quality instrument operational amplifier having a gain of approximately $10^4$. It is noted that operational amplifier may act as both the amplifier and the comparator through the differential input of the amplifier.

The amplified error voltage signal from the comparator/amplifier 29 is supplied to an analog multiplier 31 which multiplies the amplified error voltage signal by a 10 KHz sine wave signal from an oscillator 33 and produces an AC output signal having a 10 KHz frequency and an amplitude which is a function of the amplified error voltage from the comparator/amplifier 29. The output signal from the multiplier 31 provides the AC control current I to current electrodes $C_1$ and $C_2$ through an isolation transformer 35, thus completing a closed-loop automatic control system which maintains the voltage $E_v$ across the voltage electrodes $V_1$ and $V_2$ at a substantially constant potential of 0.1000 $V_{RMS}$.

The overall open-loop control factor is preferably greater than 100 db or $10^5$. Thus, the system will maintain a static error of less than $10^{-5}$ of the conductivity of standard sea water or 0.0005 mmho/cm. With a signal bandwidth of 0-1.0 KHz, it should be possible to detect over the noise level a variation of the microconductivity signal of 0.001 mmho/cm.

As discussed previously and as expressed in Equation 1, the signal current I is directly related to the conductivity of the test fluid through a gauge constant K, where K is a known function of the geometry and size of the probe. The current signal I is sensed by a scaling operational amplifier 37 whose output signal at very low impedance can be transmitted through a long cable to signal processing equipment (not shown). The signal processing equipment may calculate the conductivity of the test fluid in a conventional manner based upon the current signal I and the predetermined gauge constant K. Depending upon the particular application in which the sensor is used, the output signal of amplifier 37 can also be transmitted in either an FM mode or a digital mode. For this purpose, a voltage-to-frequency converter 38 may be provided.

Figure 9:
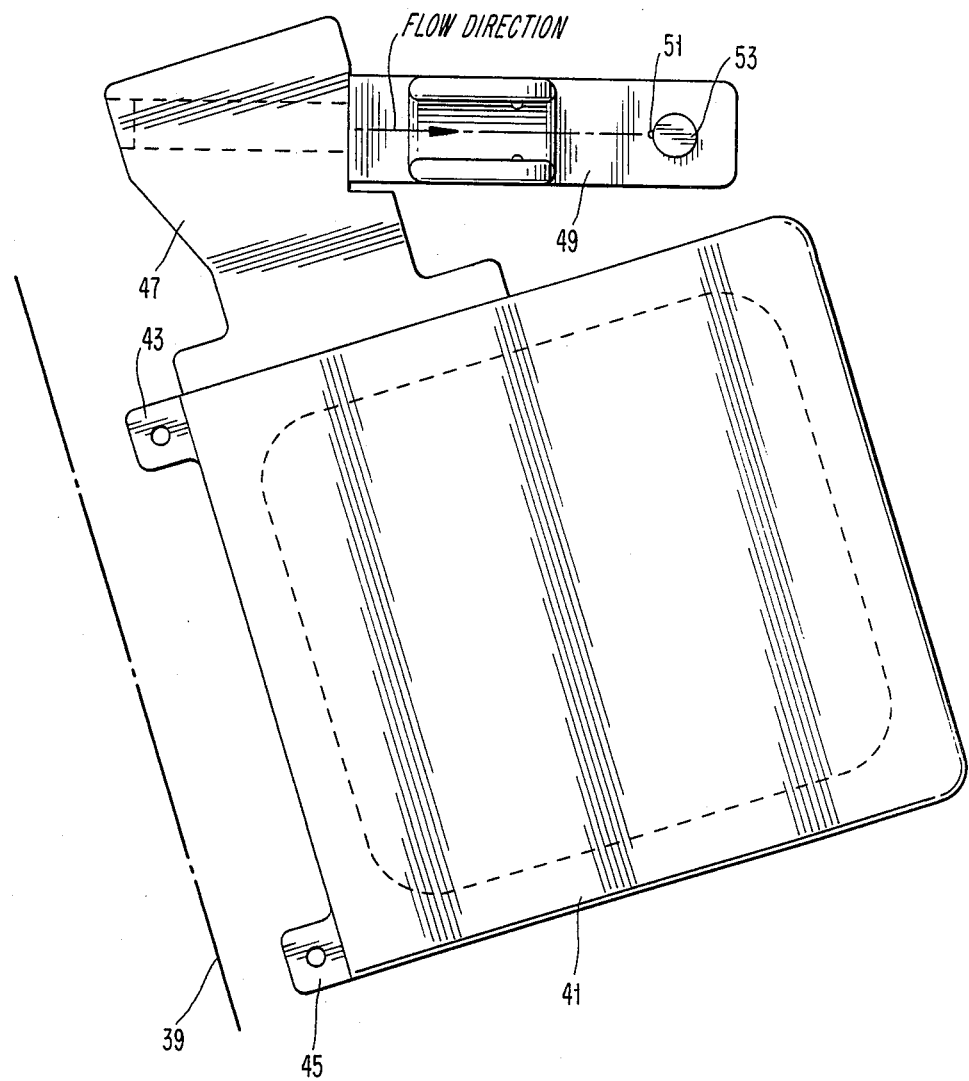
FIG. 9 illustrates a practical construction of the probe device for use in oceanic applications.

Referring now to FIG. 9, the conductivity probe of the present invention may be attached to a towing cable 39 which trails a surface ship, submarine, or other vessel. Preferably, segmented cable fairings are provided on the cable to improve flow of water over the cable as the cable is towed by the seagoing vessel. During periods when no conductivity measurements are made, the towing cable may be stored on a stowage spool located on the vessel. A housing 41 is provided for the system electronics and is attached to the towing cable 3 by suitable connectors 43 and 45. The housing 41 preferably includes an extension 47 on which a rotatable member 49 is provided. The probe 1 is mounted on the rotatable member 49. Additionally, a temperature sensor 51 may be provided on a projection 53. The water temperature may be used in conjunction with the conductivity measurement to determine the salinity of the water.

As illustrated by the broken line outline of rotatable member 49, probe 1 and projection 53, the probe may be placed in a stowage position wherein the sensor is in the same plane as the cable fairings. For the instrumented segment shown in FIG. 9, electronic housing 41 preferably serves as the cable fairing. In the stowage position, the sensor may be rolled on and off the stowage spool for the towing cable without damage to the sensor. In the deployed position, the rotatable member 49 is rotated 90° so that the probe will be outside the wake of the towing cable.

The principles, preferred embodiments and modes of operation of the present invention have been described in the foregoing specification. The invention which is intended to be protected herein, however, is not to be construed as being limited to the particular forms disclosed, since these are to be regarded as illustrative rather than restrictive. Variations and changes may be made by those skilled in the art without departing from the spirit of the invention.

What is claimed is:

1. An open-cell conductivity sensor comprising
   a first current electrode;
   a second current electrode spaced from and opposite said first current electrode, said first and second current electrodes being situated on a common axis;
   a first ring-shaped voltage electrode surrounding said first current electrode and having said common axis as a center line;
   a second ring-shaped voltage electrode surrounding said second current electrode and having said common axis as a center line;
   means for developing an alternating current across said current electrodes, and producing a potential field between said current electrodes which is sensed by said voltage electrodes; and
   means for sensing the potential across said voltage electrodes;
   said alternating current developing means being responsive to said sensing means to maintain in-phase potential across said voltage electrodes at a substantially constant value, the amount of current required to maintain said in-phase potential at a constant value being linearly proportional to the conductivity of a medium between said first and second current electrodes.

2. The sensor of claim 1 wherein said first and second current electrodes each have a hemispherical shape.

3. The sensor of claim 1 wherein said sensing means includes
   an operational amplifier having a first input connected with said first voltage electrode and a second input connected with said second voltage electrode, said operational amplifier producing an AC output signal which is a function of the in-phase potential across said voltage electrodes; and
   means for converting said AC output signal to a DC voltage signal, said alternating current developing means operating in response to said DC voltage signal to maintain the in-phase potential across said voltage electrodes at a substantially constant value.

4. The sensor of claim 3, wherein said alternating current developing means includes
   comparator means for comparing said DC voltage signal with a reference voltage and producing an error signal which is a function of the difference between said DC voltage signal and said reference voltage;
   means for generating a sine wave signal;
   multiplying means for multiplying said sine wave signal by said error signal to produce an AC current signal having an amplitude that is a function of said error signal; and
   means for applying said AC current signal across said first and second current electrodes.

5. The sensor of claim 4, wherein said applying means includes an isolation transformer.

6. The sensor of claim 3, wherein said converting means maintains in-phase potential across said voltage electrodes at a substantially constant value of 0.1000 $V_{RMS}$.

7. The sensor of claim 2, wherein the distance between said first and second current electrode is 1.000±0.005 cm.

8. The sensor of claim 7, wherein said first and second current electrodes each have a radius of 0.100±0.005 cm.

9. The sensor of claim 8, wherein said first and second voltage electrodes have a radius of 0.177±0.001 mm.

10. A four-electrode open-cell conductivity sensor comprising
 a first electrode pair including a voltage electrode and a current electrode mounted on a mounting member;
 a second electrode pair spaced from and opposite said first electrode pair and including a voltage electrode and a current electrode mounted on said mounting member;
 means for generating an electric current across the current electrodes of said first and second electrode pairs, thereby producing a potential field between said current electrodes which is sensed by said voltage electrodes, said counting member being arranged outside a primary current path of said electrical current;
 sensing means for producing a DC voltage signal which is a function of the potential across the voltage electrodes of said first and second electrode pairs; and
 comparator means for comparing said DC voltage signal with a reference voltage and producing an error signal which is a function of the difference between said DC voltage signal and said reference voltage;
 said electric current generating means operating in response to said error signal to adjust the amplitude of the current developed across the current electrodes of said first and second electrode pairs such that the potential across said voltage electrodes is maintained at a substantially constant level.

11. The sensor of claim 10, wherein said electric current generating means includes means for generating a sine wave signal and a multiplier for multiplying said sine wave signal by said error signal to generate an AC current signal which is applied to said current electrodes.

12. The sensor of claim 11, wherein said sensing means includes
 an operational amplifier having a first input connected with the voltage electrode of said first electrode pair and a second input connected with the voltage electrode of said second electrode pair, said operational amplifier producing an AC output signal which is a function of the in-phase potential across said voltage electrodes; and
 means for converting said AC output signal to said DC voltage signal.

13. The sensor of claim 12, wherein said operational amplifier has a high common mode rejection ratio and a high input impedance.

14. The sensor of claim 10, wherein said electric current generating means maintains the potential across said voltage electrodes at a substantially constant level of 0.1000 $V_{RMS}$.

15. A method for measuring the conductivity of a fluid with a four-electrode open-cell sensor including a first electrode pair mounted on a mounting member and a second electrode pair mounted on said mounting member spaced from and opposite said first electrode pair, each of said first and second electrode pairs including a current electrode and a voltage electrode, comprising the steps of
 generating an electric current across the current electrodes of said first and second electrode pairs to produce a potential field between said current electrodes, said mounting member being arranged outside a primary current path of said electric current;
 sensing the potential across the voltage electrodes and producing a DC voltage signal which is a function of the sensed potential across the voltage electrodes;
 comparing said DC voltage signal with a reference voltage and producing an error signal which is a function of the difference between said DC voltage signal and said reference voltage; and
 adjusting the amplitude of the current generated across the current electrodes of said first and second electrode pairs in response to said error signal such that the potential across said voltage electrodes is maintained at a substantially constant level.

16. The method of claim 15 wherein said current generating step generates a 10 kHz alternating current.

17. The method of claim 15, wherein said adjusting step maintains the potential across said voltage electrodes at a substantially constant level of 0.1000 $V_{RMS}$.

18. A four-electrode open-cell conductivity sensor comprising
 a first electrode pair including a voltage electrode and a current electrode;
 a second electrode pair spaced from said first electrode pair and including a voltage electrode and a current electrode;
 means for generating an electric current across the current electrodes of said first and second electrode pairs, thereby producing a potential field between said current electrodes which is sensed by said voltage electrodes;
 sensing means for producing a DC voltage signal which is a function of the potential across the voltage electrodes of said first and second electrode pairs; and
 comparator means for comparing said DC voltage signal with a reference voltage and producing an error signal which is a function of the difference between said DC voltage signal and said reference voltage;
 said electric current generating means operating in response to said error signal to adjust the amplitude of the current developed across the current electrodes of said first and second electrode pairs such that the potential across said voltage electrodes is maintained at a substantially constant level;
 said electric current generating means including means for generating a sine wave signal and a multiplier for multiplying said sine wave signal by said error signal to generate an AC current signal which is applied to said current electrodes.

19. The sensor of claim 18, wherein said sensing means includes
 an operational amplifier having a first input connected with the voltage electrode of said first electrode pair and a second input connected with the voltage electrode of said second electrode pair, said operational amplifier producing an AC output signal which is a function of the in-phase potential across said voltage electrodes; and means for converting said AC output signal to said DC voltage signal.

20. The sensor of claim 19, wherein said operational amplifier has a high common mode rejection ratio and a high input impedance.

* * * * *